United States Patent [19]

Pirlet

[11] Patent Number: 4,601,762
[45] Date of Patent: Jul. 22, 1986

[54] METHODS FOR CONDITIONING METAL PRODUCTS

[75] Inventor: Robert A. Pirlet, Embourg, Belgium

[73] Assignee: Centre de Recherches Metallurgiques-Centrum voor Research in de Metallurgie, Brussels, Belgium

[21] Appl. No.: 654,005

[22] PCT Filed: Jan. 13, 1984

[86] PCT No.: PCT/BE84/00001
§ 371 Date: Sep. 14, 1984
§ 102(e) Date: Sep. 14, 1984

[87] PCT Pub. No.: WO84/02860
PCT Pub. Date: Aug. 2, 1984

[30] Foreign Application Priority Data

Jan. 20, 1983 [BE] Belgium ................................ 47767

[51] Int. Cl.⁴ ................................................. B23K 7/06
[52] U.S. Cl. ............................................ 148/9.5; 266/51
[58] Field of Search ........................ 148/9.5; 266/51, 80

[56] References Cited

U.S. PATENT DOCUMENTS

| | | |
|---|---|---|
| 3,953,943 | 5/1976 | Nakaoka . |
| 3,992,826 | 11/1976 | Nakaoka et al. . |
| 4,120,703 | 10/1978 | Engel ............................... 148/9.5 |
| 4,131,490 | 12/1978 | Oishi et al. .......................... 148/9.5 |
| 4,175,729 | 11/1979 | Karlsson ............................. 266/51 |
| 4,336,923 | 6/1982 | Shiraiwa et al. ..................... 266/51 |
| 4,337,099 | 6/1982 | Hiroshima et al. .................. 148/9.5 |

FOREIGN PATENT DOCUMENTS

| | | |
|---|---|---|
| 0053274 | 11/1980 | European Pat. Off. . |
| 0030976 | 7/1981 | European Pat. Off. . |
| 1033168 | 7/1958 | Fed. Rep. of Germany . |
| 2529154 | 1/1976 | Fed. Rep. of Germany . |
| 2606853 | 8/1977 | Fed. Rep. of Germany . |
| 2843269 | 4/1980 | Fed. Rep. of Germany . |
| 69006 | 2/1974 | Luxembourg . |

OTHER PUBLICATIONS

"The Modern Way—Automatic Inspection and Conditioning of Billets and Blooms", George N. Villee, *Iron and Steel Engineer,* vol. 55, No. 5, May 1978, pp. 44–48.

Primary Examiner—Melvyn J. Andrews
Attorney, Agent, or Firm—Holman & Stern

[57] ABSTRACT

The surface and/or subsurface defects of the surface to be treated are detected, preferably over the entire said surface. The defects are eliminated by scarfing with a torch and/or by milling, following which the treated surface is inspected and cleaned. The detection, elimination, inspection, and cleaning devices are maneuvered by means of programmable robots or automatons controlled by a computer. The process may be applied on-line to hot, moving products (e.g., rolled or continuous cast products).

6 Claims, 1 Drawing Figure

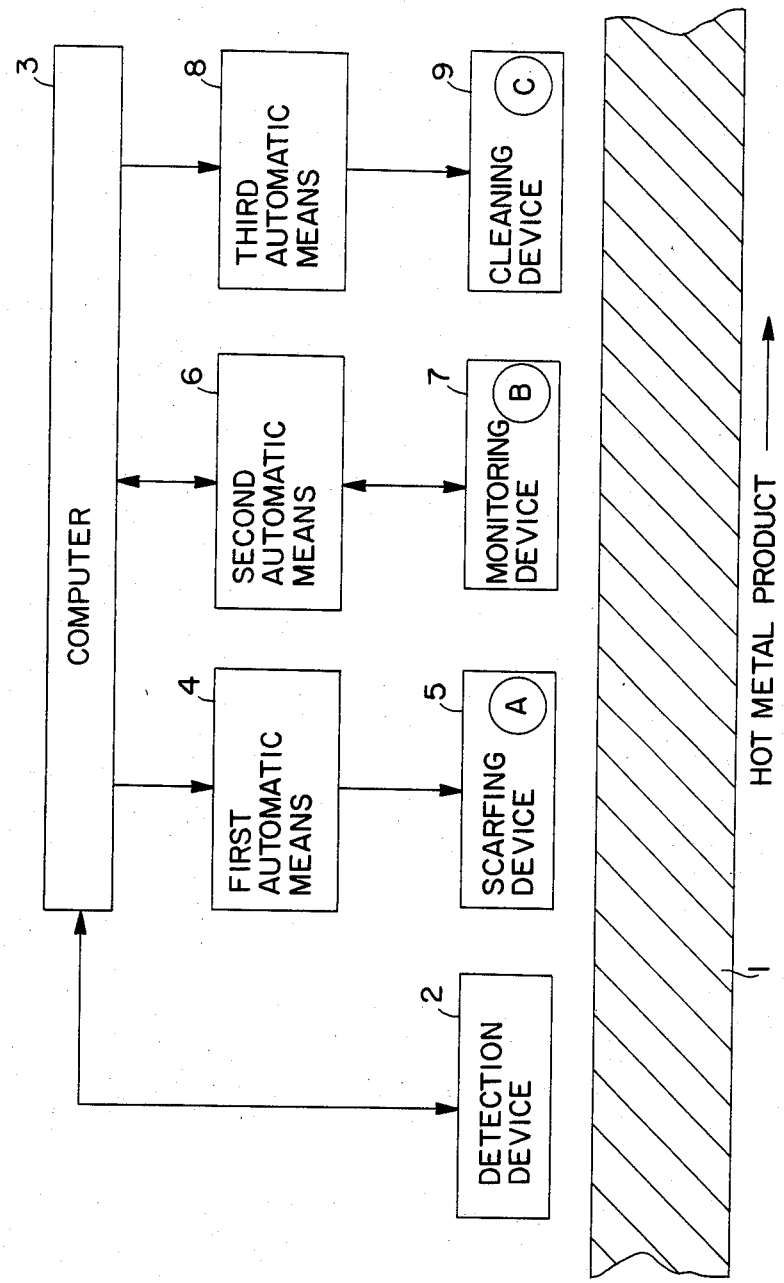

METHODS FOR CONDITIONING METAL PRODUCTS

CROSS REFERENCE TO RELATED APPLICATION(S)

The invention described in this application is described in PCT Application No. PCT/BE84/00001, filed Jan. 13, 1984 on which Applicant is claiming priority under 35 USC 1.119.

BACKGROUND OF THE INVENTION

The invention relates to an improved method for treating metal products. It applies in particular to heat treating of products obtained by rolling or continuous casting, such as steel slabs.

The term "treatment" when applied to metal products generally refers to sets of different operations usually comprising examination of the product with a flaw detector, elimination of the detected flaws, monitoring of said elimination, and possibly a final cleaning of the product.

The treatment proposed by the present invention relates to surface and subsurface ("subcutaneous") defects, i.e., defects disposed at depths not exceeding 10 mm from the surface of the product.

In the following description, reference is made in particular to continuous cast steel slabs. Obviously, the description is in no way limiting in character; the inventive method may equally be applied to numerous other metal products.

Steel works have always striven to produce products with minimum defects, so as to ensure finished products of high quality. However, to date it has not been possible to produce slabs which are complete free of defects. Consequently there is a need to detect and eliminate the kinds of defects which may be detrimental to the quality of finished products.

Treatment techniques currently employed are mostly empirical in nature, and their effectiveness tends to be dependent on the skill and experience of the operator.

One method in particular is known according to which the slab is cooled and a zone along the longitudinal axis on the top face of the slab is scarfed with a torch. This scarfed zone is generally not more than 5 mm deep and is 50 to 60 mm long. When the torch flame encounters a defect its shape and luminous intensity are altered momentarily; the operator must interpret these changes in order to assess the nature and degree of the defect.

In the case of certain very high quality steels, an additional two zones are sometimes scarfed, disposed near the longitudinal edges of the slab, parallel to the scarfed zone which was executed on the logitudinal axis.

In either case, the quality of the entire surface is assessed by extrapolating the results obtained by scarfing the zone(s) on the top face of the slab.

This method is very slow, and its empirical nature stands in the way of attainment of objective and reproducible results. Moreover, it basically only covers a small part of the surface of the product, and thus does not provide any real, practicable information concerning the rest of the surface.

There is also known a point scarfing apparatus, employed when gross defects are sought to be eliminated. A frame or carriage bearing a certain number of torches is displaced automatically along the slab to be treated, and the torches clean the surface by their action (scarfing, flame chipping, descaling, torch deseaming, etc.), at locations the coordinates of which are communicated to the control means of the said apparatus.

However, in order to use this apparatus, one must previously have located the defects which are to be eliminated. Furthermore, the apparatus does not allow the treated zone or the scarfing operation itself to be inspected; thus one suffers the hazards of operating blind.

A more recent method, applicable to products maintained at a temperature of 800° to 1000° C., consists of scarfing a zone of the type indicated supra, and transmitting the image of the flame of the torch to a remote location, with the aid of a television camera and monitor. The operator may thus observe the flame without being exposed to the heat emitted by the product at high temperature. The method gives the coordinates (the positions in the said zone) of the defects as indicated by the variations in shape and luminosity of the flame. The hot product is then conveyed to a treatment stand, where an automatically controlled (second) torch eliminates the defects at points the coordinates of which are communicated to the control means of the said automatic torch.

This method has the disadvantages inherent in the scarfing method discussed supra, namely slowness, empirical nature, lack of reliability and reproducibility of the observations, and small extent of the part of the surface observed. Furthermore, there is the inherent disadvantage of separation of the operations of detection and defect-elimination, as a result of which substantially more floor space and processing time are required, with attendant greater cost of the operation.

In addition, current treatment methods are essentially discontinuous, since in most cases they require that the product be transferred into an appropriate workshop (called a "treatment shop") which is separate from the casting room. This discontinuity disadvantage is the more serious as a greater proportion of the steel produced is continuously cast.

SUMMARY OF THE INVENTION

An object of the present invention is a process which enables one to alleviate the various disadvantages aforesaid.

In particular, the inventive method enables the various operations which comprise the treatment of a metallic product such as a continuous-cast steel slab (ingot) to be combined at a single location, said operations being namely detection of defects, elimination of these defects, and control of the surface of the metal product which is to be subjected to treatment.

A second object of the invention is to provide a treatment method which is applicable to moving metal products, e.g. which can be applied as closely as possible to the exit point of the installation on which the product is formed.

Toward this end, the inventive metal product treating method, wherein the surface and/or subsurface defects are detected and are eliminated by a device which is itself known, is carried out preferably by scarfing with a torch and/or by milling, is essentially characterized in that, preferably acting on a moving product which is exiting a continuous casting installation, detection means are automatically passed along at least one face of said product; in that the defects present in said face are detected; in that data indicating the location and/or seriousness of the defects detected are collected and introduced into a computer; and further in that said computer is employed to govern at least one automatic control system which provides for the positioning and operation of a device for eliminating the defects, further to govern at least one automatic control system equipped with means for monitoring the elimination of said defects, and further to govern at least one automatic control system equipped with means for cleaning the surface of the said product.

According to an advantageous embodiment of the inventive method, the operation for eliminating the defect is repeated if the subsequent monitoring indicates that the defect was not completely eliminated in the first operation.

If the defect is still visible at a depth of about 5 mm, the operation of defect elimination is interrupted and the and the defective product piece is downgraded.

According to the invention, it is particularly advantageous for the method to be employed on-line, to a metal product which is moving.

According to another advantageous embodiment of the invention, a torch flame is moved along the surface to be treated, the image of said flame is analyzed by means which are themselves known, in order to detect the variations in the characteristics of the flame due to the presence of defects, data are generated from the analysis of the images which data represent the seriousness and location of the defects, these data are transmitted to a computer, and by means of this computer and on the basis of said data the action of the automatic control systems described supra is controlled, to provide elimination of the said defects, and monitoring and cleaning of the product surface.

In this connection it has been found particularly advantageous to perform the analysis of the said images by detecting the variations in the luminous intensity of the flame compared to a reference level corresponding to the absence of defects.

It has been found particularly advantageous, in this embodiment to employ the same torch used to detect the defects to eliminate said defects. In this case, the movement of the torch is interrupted at any point where the analysis of the image shows a deviation between the instantaneous image and the reference image which deviation exceeds a predetermined value, and this interruption of the movement is continued as long as the said deviation remains above the said predetermined value.

The preferred technique for detecting the defects in the product is by successive passes, preferably transverse passes, in a back and forth movement with respect to the surface.

According to the invention the detection of the defects may be accomplished either by examining the entirety of the surface to be treated or by examining only a part of the surface and extrapolating the results of this partial examination to the entire surface to be treated, the extrapolation being by means of an algo- rithm [sic] based on industrial practice.

According to the invention it has been found advantageous to detect and eliminate the defects on at least two faces of the product, wherewith the operations may be carried out simultaneously on the different faces of the product, but need not be carried out simultaneously.

According to an particularly advantageous embodiment of the method of the invention, at least one of the automatic control systems is a programmable robot or automaton.

The invention may be accomplished by known means for the operations of detection of defects, elimination of defects, monitoring of the product surface, and cleaning of the product surface.

For example, the following devices may be used:

an electro-optical system such as a television system, to detect the surface defects;

a Foucault current device to detect subsurface defects;

a milling machine or a torch, to eliminate the defects;

a television system with monitor to monitor the surface; and a scraper to clean the surface.

The inventive method enables one to inspect and treat one or more entire faces of the metal product. Thus it is not subject to the major risk of error which attends the customary methods which employ extrapolation from limited monitoring.

Further, the inventive method is based on an objective detection technique, preferably automatic, for determining the location and seriousness of defects. Being objective, the technique is reproducible, and its effectiveness does not depend on the skill or experience of the operator.

Finally, the inventive method may be employed in a continuous mode, simultaneously (or not) on one or more faces of the metal product. This flexibility allows the number of manipulations to be reduced, does not require a special treatment-workshop separate from the rolling or casting room, and greatly reduces the time required for the operations involved.

In the case of continuous cast slabs (ingot), the invention may be applied following the exit of the slab from the casting machine. This enables reliable information on the quality of the slab to be obtained very quickly. In particular, it enables one to determine which slab pieces must be downgraded or rejected at the time of oxygen i.e., torch cutting.

BRIEF DESCRIPTION OF DRAWING

The single drawing FIGURE is a block diagram illustrating the inventive method.

DESCRIPTION OF PREFERRED EMBODIMENT

Referring to the encompanying drawing, a scanning detector measures the coordinates (xy) and the depth of a defect in a scanned face of a moving slab. The data concerning the coordinates and depth of the defect is introduced into a computer which controls the positioning and operation of a defect removal means A, the inspection of the scarfed area by means of an inspection device B and the cleaning of said area by means of a scrapper C. When the inspection device B shows that the scarfing is unsatisfactory, the device informs the computer which re-initiates the cycle of defect removal and inspection. The scrapper C operates only in the scarfed areas, under the control of the computer.

The scanning detector is shown in the FIGURE as detection device 2, which supplies information to, and receives information from, a computer 3. The slab 1 is a moving hot metal product to be scanned; and which may have defects to be corrected. The slab 1 moves in the direction of the arrow shown in the FIGURE.

The computer 3 controls operation of the scarfing device via a first automatic means 4. The scarfing device 5 is the defect removal means A.

The scarfed slab 1 is then inspected by an inspection device B, shown in the FIGURE as monitoring device 7. The monitoring device 7 communicates with the computer 3 via a second automatic means 6.

The scraper C, shown in the FIGURE as cleaning device 9, operates only in the scarfed areas under the control of the computer via the third automatic means 8.

I claim:

1. A method of treating a moving hot metal product comprising inspecting at least one face of the metal product by automatically displacing a detection device along said face, using said detection device to detect defects present in the product and to generate data concerning the coordinate location and depth of said defects, introducing said data into a computer, and using said computer for controlling:

a first automatic means to position a scarfing device at a location where a defect has been detected and to operate the scarfing device for a time necessary to remove the defect;

scarfing the defect;

a second automatic means which monitors the removal of the defect;

and a third automatic means which cleans the product surface;

at least one of said first, second, and third automatic means comprising a programmable robot.

2. The method of claim 1 wherein in the step of using said detection device, said detection device comprises a torch flame, and said torch flame is used to detect the defects by analyzing a flame image to detect variations in characteristics of said flame image caused by the presence of a defect in the product.

3. The method of claim 2 wherein in the step of using said detection device, movement of said torch flame is interrupted at location where an analysis by said computer of said flame image shows a deviation between an instantaneous image and a reference image when said deviation exceeds a predetermined value, and movement of said torch is resumed when said deviation returns to a value less than said predetermined value, the coordinates of said points being introduced to the computer.

4. The method of claim 1 wherein in the step of using said detection device, the detection of defects is accomplished by examining at least a part of the surface to be treated, and extrapolating results of the examination to the remaining, non-examined portion of the surface.

5. The method of claim 2, further comprising the step of repeating operation of said scarfing device at a location monitored by said second automatic means under control of said computer when said second automatic means indicates to said computer that the defect to be removed was not completely eliminated by previous operation of said first automatic means.

6. The method of claim 2 wherein movement of the torch is interrupted at points where the analysis of the image shows a deviation between instantaneous image and reference image which deviation exceeds a predetermined value, and movement of the torch is resumed when the deviation returns to a value less than said predetermined value, the coordinates of said points being introduced to the computer.

* * * * *